United States Patent [19]

Batchelder

[11] Patent Number: 5,052,405
[45] Date of Patent: Oct. 1, 1991

[54] METHOD AND APPARATUS FOR MEASURING THE DENSITY OF AN OBJECT INCLUDING A LIVING BEING

[76] Inventor: J. Samuel Batchelder, Campbell Dr., Somers, N.Y. 10589

[21] Appl. No.: 387,287

[22] Filed: Jul. 27, 1989

[51] Int. Cl.⁵ ............................................ A61B 5/103
[52] U.S. Cl. .................................. 128/774; 73/32 R; 73/433
[58] Field of Search ...................... 73/32 R, 433, 149; 128/774

[56] References Cited

U.S. PATENT DOCUMENTS

| | | |
|---|---|---|
| 3,455,168 | 7/1969 | Taylor et al. . |
| 3,487,698 | 1/1970 | Leger, Jr. et al. . |
| 3,557,625 | 1/1971 | Leger, Jr. et al. . |
| 3,769,834 | 11/1973 | Fletcher et al. . |
| 4,144,749 | 3/1979 | Whitmore . |
| 4,144,763 | 3/1979 | Vogelman . |
| 4,184,371 | 1/1980 | Brachet . |
| 4,449,406 | 5/1984 | van Haren . |
| 4,831,527 | 5/1989 | Clark .................................. 128/774 |

Primary Examiner—Randall L. Green
Assistant Examiner—K. Reichle
Attorney, Agent, or Firm—Mark P. Stone

[57] ABSTRACT

A method and apparatus is provided for measuring the volume and density of an object, including a living being, which avoids the necessity of immersing the subject in a liquid medium. Where the subject is a living being, the percentage of body fat may readily be determined from the density value. The density of the subject is measured by recording the weight of the subject for several different temperatures of a fluid, preferably air, surrounding the subject. The apparent weight change of the subject at the different measured temperatures of surrounding air represents changes in the buoyant forces exerted by the air on the subject at different air densities. The buoyant force acting on the subject is calculated from these measurements, and the volume of the subject is determined from its relationship with the buoyant force. The density of the subject can then be calculated from the volume and weight parameters. Where the subject is a human being or animal, its density is monotonically related to its fat content.

30 Claims, 2 Drawing Sheets

I. HEATING CYCLE
10 SECONDS

FIG. 2b

II. WARM WEIGHING
10 SECONDS

FIG. 2c

III. COOLING CYCLE
10 SECONDS

FIG. 2d

IV. AMBIENT WEIGHING
10 SECONDS

METHOD AND APPARATUS FOR MEASURING THE DENSITY OF AN OBJECT INCLUDING A LIVING BEING

BACKGROUND OF THE INVENTION

It has long been known that the volume of an object, including living matter, may be measured by immersing the body in a liquid medium and measuring the quantity of liquid displaced. The ratio of the weight of the subject to its volume, as measured by the volume of the displaced liquid, determines the density of the subject. Density measurement using immersion techniques are commonly used to detect flaws or defects such as voids in various methods. The density of a material having voids will be less than the known density of the pure material.

It is also well known that the density of living matter or tissue is directly related to its fat content—the leaner the body, the greater its density. However, it is apparent that known immersion methods for measuring density are impractical and awkward when employed to measure the density or fat content of a living being since an essential step of the procedure is to immerse the subject in a liquid medium.

The immersion procedure also has drawbacks even when employed to measure the volume or density of non-living objects. For example, the observed density of porous subjects will change when immersed in a liquid because fluid fills pores and voids which are intended to be detected by the measurement. Moreover, certain materials may be damaged by immersion in liquid, and others may be physically awkward to immerse.

Other known methods and apparatus for determining density also have distinct disadvantages. U.S. Pat. No. 3,455,168 is directed to the measurement of fat content of animal tissue, and advocates placing compressed slugs of meat and fat mixtures of known volume on mechanical weighing mechanisms. Counterweights and spring compensators are used to mechanically convert the measured density to fat content, compensating for the temperature of the sample, the type of meat, and its source on the animal. However, the patent assumes that the volume of the tissue being examined is a known parameter, and thus discloses no means for measuring the volume.

U.S. Pat. No. 3,487,698 is similar to the aforementioned patent and includes automatic and sequential measurement of volume, weight and temperature of a meat sample. A computer determines the density from the volume and weight measurements, and determines a standard fat content for the specific kind of meat having that density, and then corrects the fat content for variations in the temperature of the meat. Different mechanisms are used for volume and weight measurements, and the temperature measurement is that of the meat sample and not of the ambient air.

U.S. Pat. No. 3,557,625 analyzes the fat content of a meat sample by compressing it with a piston to compute the volume, injecting probes to measure the temperature, and thereafter computing the fat content from measured parameters. The weight and volume are measured with two different apparatus. The temperature measurements are those of the meat sample, and not of the ambient air.

U.S. Pat. No. 3,769,834 discloses a method and apparatus for measuring the changes in volume of a human being under near zero gravity conditions. The subject is placed in a sealed cylinder, and a piston is used to compress the remaining gas in the cylinder by a known volume. By observing how the pressure in the chamber changes with the motion of the piston, the volume of the body can be determined. It is conceptually distinct from the method and apparatus of the invention to be disclosed herein. In the known patent, pressure is varied while temperature is held roughly constant. On the contrary, the method and apparatus of the present invention hold the pressure constant and vary the ambient temperature. Moreover, the method of volume measurement disclosed by the known patent is obviously unsuitable for wide scale application since it is carried out under near zero gravity conditions.

U.S. Pat. No. 4,144,749 discloses an example of a known method of hydrostatic measurement of the volume of a human body by immersing the subject in a tank of water, and determining the volume of the subject from the quantity of water displaced.

U.S. Pat. No. 4,144,763 discloses a volumetric apparatus for measuring body fat in which gas is compressed into a sealed chamber, the subject is placed in an adjacent chamber at room temperature, the chamber enclosing the subject is sealed, a valve connecting the two adjacent chambers is opened, and the air pressure in the adjacent chambers is measured. The volume is determined by varying the pressure of the air and not by any temperature variation thereof. The temperature is allowed to stabilize before pressure measurements are taken, and the volume is calculated from differences in pressure.

U.S. Pat. No. 4,184,371 discloses an apparatus for measuring the volume of a body by pressurizing a sealed chamber containing the body with a known displacement of air. Differentials in temperature of the ambient air are not employed in the volume measurement. The patent further discloses the application of time modulated pressure in the form of sub-sonic waves, and the use of a parallel chamber to measure volume by nulling differential pressure.

U.S. Pat. No. 4,449,406 discloses a method and apparatus used to measure the fat content of animal meats. Samples of the meat in a processing plant are first weighed, and then compressed in a piston to determine the volume, and thereafter are measured by a thermocouple to determine the temperature of the meat. The density of the sample is calculated from the weight and volume measurements, and a computer determines the fat content based upon the density. The temperature measurement of the meat is used to correct for temperature dependence in the known density/fat content relation. The temperature parameter is not used in the volume measurement.

There are several other body composition measurement techniques that have been implemented with varying degrees of success. The hydrostatic density or volume measurement is generally considered the most accurate technique available today. The most common technique is the fat fold caliper. [Jackson, A. S., and Pollock, M. L., "Generalized equations for the prediction of body composition", *Medicine and Science in Sports*, 10: 47, 1978.] The concept here is that fat is generally stored by the body just under the skin, partly as thermal insulation. By pinching folds of skin at various places on a body, a general idea of the body's composition can be obtained. In a similar way, taking ratios of measurements of different parts of the body can infer the amount of fat stored under the skin. [Davis, P. O., and Dotson, D. O., "Development of simplified techniques for the determination of percent body fat in adult males", *The Journal of Sports Medicine and Physical Fitness*, Vol. 25, pp. 255-261, 1985.]

There are references to other techniques, such as measuring the rate that infrared light is diffused by the skin. [Conway, J. M., Norris, K., and Bodwell, C. E., "A new approach for the estimation of body composition: infrared interactance", *American Journal of Clinical Nutrition*, Vol. 40, 1984.] A known device measures the fat content of hogs and cattle by measuring ultrasonic reflectivity.

It is apparent from the above discussion that none of the aforementioned patents or known techniques disclose a method or apparatus for calculating density and body fat using a single apparatus which simultaneously weighs the subject and calculates its volume. Moreover, none of the above patents or techniques suggest a method of calculating the volume of a human subject by varying the temperature of the ambient air (and thus varying the buoyant force exerted on the subject by the air), and thereafter calculating the volume from the buoyant force determined from the differences in the apparent weight of the subject at different ambient air temperatures. On the contrary, the methods and apparatus for calculating fat density of a human or animal subject disclosed by the aforementioned prior art patents include immersing the subject in a liquid bath; sealing the subject in a closed chamber at near zero gravity conditions; or varying air pressure in a sealed chamber.

It is the primary object of the present invention to provide an improved method and apparatus for efficiently and expeditiously determining the weight, volume and density of an object, and in particular a non-invasive method and apparatus for measuring the fat content of a living being. Other aspects and objects of the invention will be apparent from the following discussion.

SUMMARY OF THE INVENTION

In accordance with the present invention, a method and apparatus is provided for the non-invasive measurement of weight, volume and density of an object. In particular, where the subject is a living being or living tissue, the method and apparatus will calculate the fat content which is directly related to the density of the subject.

The subject to be measured is preferably, but not necessarily, placed in a closed booth and immersed in a bath of gas, preferably ambient air, at a predetermined temperature at ambient barometric pressure and a first weight measurement is made. Thereafter, the initial air bath is evacuated and replaced by an air bath at a second predetermined temperature which is different from the first predetermined temperature. The weight of the subject is then measured at the second predetermined temperature, and the second recorded weight will be different from the first recorded weight as a result of the change in buoyant force of the air acting on the subject. The change in the buoyant force exerted by the air occurs from the change in the density of the surrounding air which itself results from the change in the air temperature. The difference in the two apparent measured weights corresponds to the change in the buoyant force exerted by the air on the subject. The buoyant force exerted on the subject is proportional to the volume of the subject multiplied by the density of the air. The density of the air at each temperature may be determined from the temperature and barometric pressure of the air. Therefore, the volume of the subject, which remains constant, can then be determined from the differences in measured buoyant forces exerted at the different temperatures and the difference in the density of the air at the different temperatures. The density of the subject is determined by the ratio of the subject's weight at ambient temperature and pressure conditions to the subject's volume as measured in accordance with the aforementioned procedure. Where the subject is a living being or animal, the measured density can be related to a corresponding fat content.

Although the above-described method is preferably carried out in a closed housing, it is within the scope of the invention to take the temperature and weight measurements in an open environment. This may be accomplished by blowing air at different temperatures at the subject, rather than completely surrounding the subject in a bath of air. It is beneficial for the wind loading in this configuration to be horizontal.

Preferably, several different weight measurements of the subject are taken at several different ambient air temperatures to compensate for system drifts, sweating of the subject, air currents, structure creep, and other factors which may cause variations in the measurements. Moreover, when the subject is a living being, normal respiration or breathing will cause significant changes in the average body volume and density. Preferably, the method and apparatus of the present invention will compensate for these fluctuations in body volume by considering cyclical changes in the apparent density of the subject with a time constant approximately equal to the respiration rate of the subject to obtain an average volume measurement for each temperature differential.

DESCRIPTION OF THE BEST MODES FOR CARRYING OUT THE INVENTION

Figure 1:
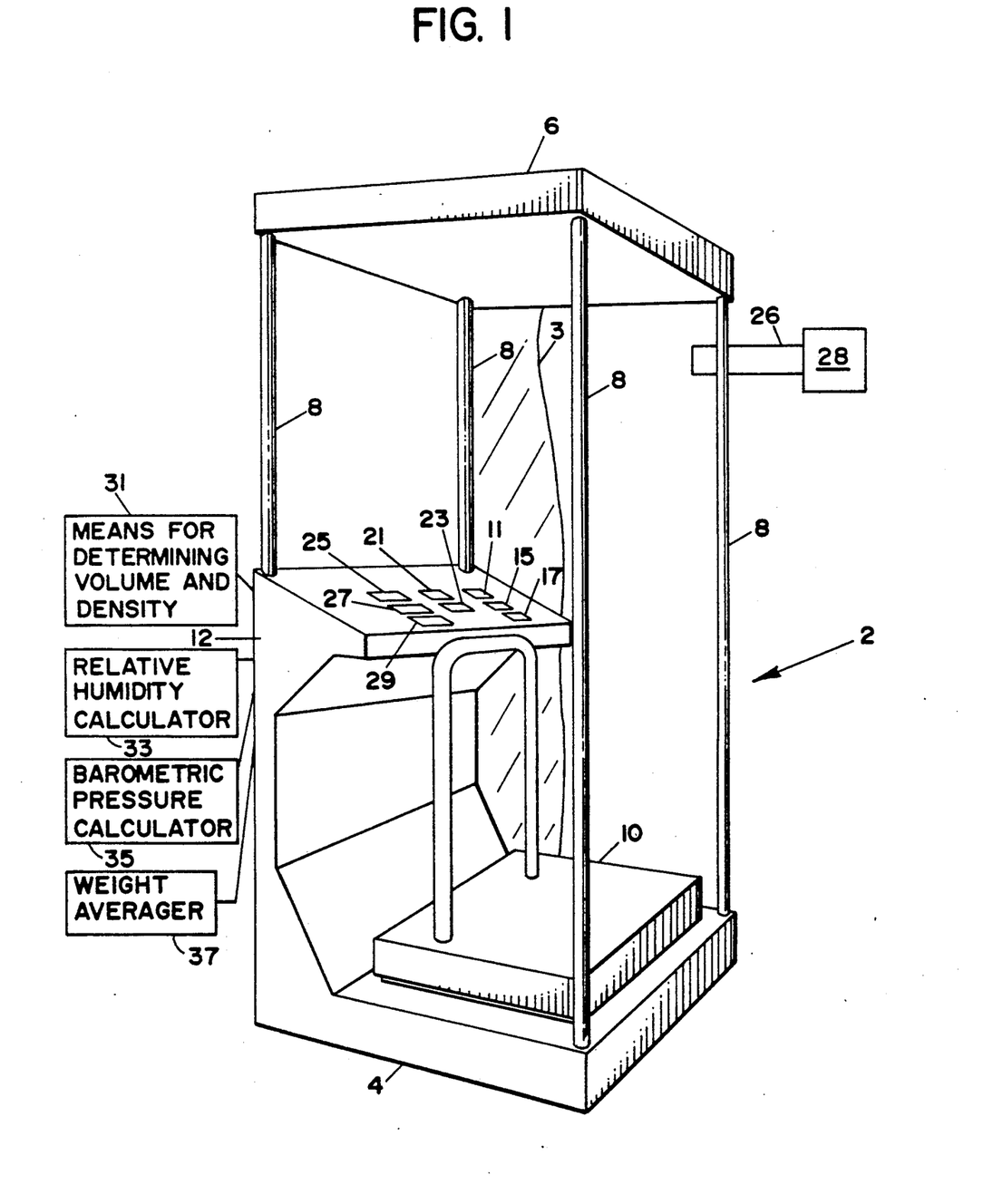
FIG. 1 of the drawings illustrates a perspective view of one embodiment of an apparatus in accordance with the present invention.
Figure 2A:
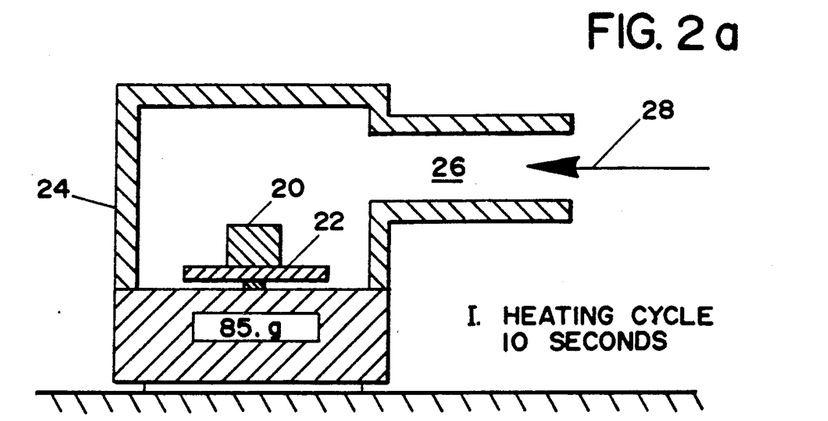
FIG. 2 of the drawings illustrates a schematic flow chart showing different sequential steps of the method of the present invention.
Figure 2B:
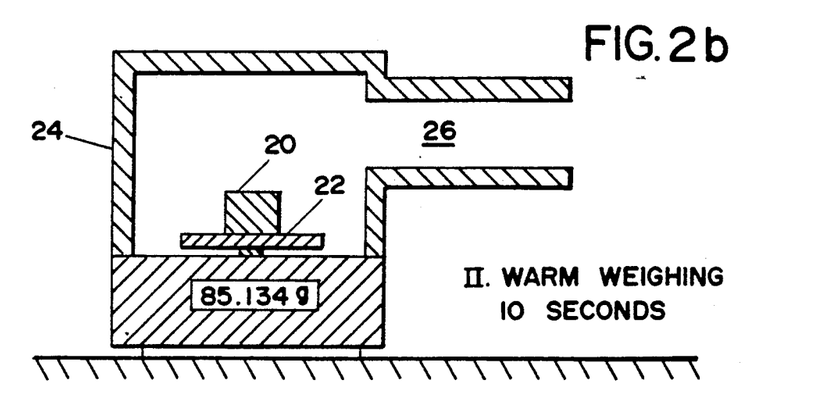
Figure 2C:
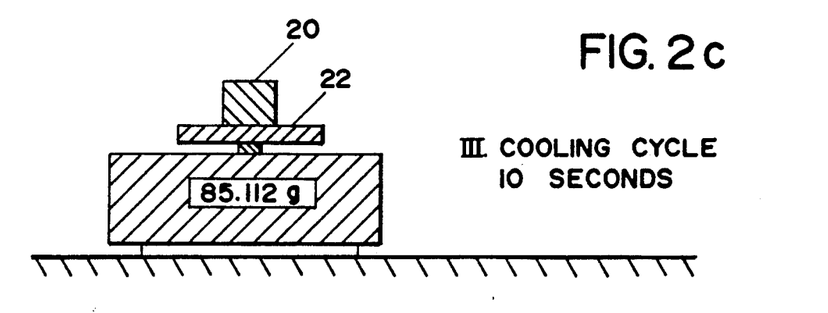
Figure 2D:
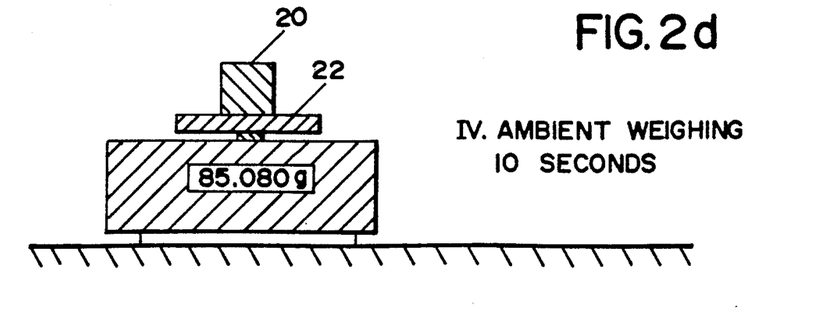

FIG. 1 of the drawings illustrates a first embodiment of the present invention generally disclosing an open booth designated by the reference numeral 2. The booth 2 includes a base 4, a top 6, and four supporting side columns 8. A floor scale 10 is supported by the base 4, and a display panel 12 is mounted within the booth 2 at a position where it is readily observable by a subject standing upright on the scale 10. The display panel 12 includes a temperature sensor 11, a volume display 15, a weight display 17, a density display 21, a relative humidity display 23, a barometric pressure display 25, a fat content display 27, an average weight display 29, means 31 for determining the volume and density of an object, means 33 for calculating relative humidity, means 35 for calculating barometric pressure, and means 37 for averaging weight measurements of an object. The booth further includes means for introducing a gas, such as air, at a temperature differing from the ambient air temperature in the booth (either hotter or colder) into the booth.

These means may include a conduit or tube 26 coupled at one end to a source 28 of hot or cold air and having a discharge opening leading into the booth 2 or a measuring chamber 24 (as illustrated in FIG. 2). Means for evacuating the heated or cooled air injected into the booth (not shown in the drawing), such as a fan or blower, may also be provided within or proximate to the booth. The booth 2 also includes a closure element 3, such as a wrap around curtain to selectively cover the open sidewalls of the booth.

The present invention operates on the principle that objects and people are immersed in a bath of air at all times, and that the density of the ambient air surrounding an object or person may be readily changed by changing the temperature of the air. If an object or person is weighed at two different ambient air temperatures, the apparent measured weights will be different. This difference results from the fact that warmer air is less dense than colder air, and accordingly exerts less of a buoyant force on an object or a person than colder air, making the object or person appear to weight more in hotter air than in colder air. The difference in the apparent weight of the subject corresponds to the difference in the buoyant forces exerted on it by the colder and hotter air. The buoyant force exerted on the subject is equal to the volume of the subject multiplied by the density of the surrounding air. Since the volume of the subject remains constant and the density of air at different temperatures are known or readily determinable quantities, the differences in the apparent weight at different densities of air may be used to determine the constant volume of the subject based upon the aforementioned relationship between the volume, air density and buoyant force. That is, the difference in the apparent measured weights (i.e., difference in buoyant force exerted) is proportional to the difference in air densities multiplied by the constant volume of the subject. The density of the subject (its weight (at ambient)) divided by the calculated volume) is monotonically related to the fat content of tissue when the body being measured is a human being. The leaner that the body is, the greater its density is.

It is evident that the volume and density calculations made in accordance with the method and apparatus of the present invention can be made by simply varying the temperature of the ambient air surrounding the subject to be measured. The method is economical because it takes all necessary measurements in a pre-existing environment, namely, the surrounding air. By employing the ambient air as the only medium in which measurements are taken, the awkward procedure involved in using liquid immersion techniques is avoided. Moveover, the ambient air environment does not adversely affect the density measurement (as does liquid immersion when used to measure articles having voids or flaws), and will not damage or otherwise adversely affect the vast majority of potential materials to be measured.

Referring back to FIG. 1 of the drawings, a human subject to be measured steps inside the booth 2 (or a non-living subject is placed within the booth 2) which is at ambient temperature, pressure, and relative humidity. An initial weight measurement is taken on the scale 10 and recorded on the display panel together with the pressure, temperature and relative humidity readings. Thereafter, the booth is enclosed, as for example by drawing curtains around the open sidewalls, to define a closed structure. Air, at a temperature different from ambient, is introduced into the closed structure for the purpose of changing the ambient air temperature surrounding the subject being measured. The temperature, pressure, and relative humidity, together with the apparent weight of the subject on the scale at the changed air temperature, is measured and displayed on the display panel 12. As discussed above, the difference in the apparent weight of the subject at different ambient temperatures, together with the difference in the ambient temperatures themselves, are used to calculate the volume and the density of the subject. The relationships between density of the surrounding air, changes in ambient temperature, changes in buoyant forces exerted on a subject by the ambient air, and the volume and density of the subject, are more fully illustrated and disclosed in the attached Appendix, which forms part of this specifications.

The above-described measuring procedure has been described as employing air at a temperature different from ambient to calculate the density of the subject. However, it is clearly within the scope of the invention to use gases other than air for this purpose. (Air is, or course, the preferred medium because of its abundant supply.) Moreover, although the procedure described above encloses the subject to be measured within an enclosed structure or booth, the calculations may also be made in an open area by merely blowing hot or cold air on a subject on a scale proximate to temperature sensors.

FIG. 2 of the drawings illustrates a flow chart of a typical operating sequence of the apparatus of the present invention. Step I places an object 20 of unknown density on a scale 22 enclosed within a measuring chamber generally illustrated by reference numeral 24. The weight of the unknown object is measured and recorded. The air temperature, relative humidity and pressure within the chamber are initially at ambient as a result of the open inlet passageway 26 leading into the chamber. Thereafter, a source 28 of heated air at a temperature of about 140 degrees Fahrenheit is fed into the chamber 24 through the passageway 26 for approximately 10 seconds, raising the ambient air temperature surrounding the object 20 to about the temperature of the injected air. In the present example, the volume of air contained within the chamber 24 is approximately 10 liters. It is apparent that the heating time necessary to heat the surrounding air to the temperature of the injected air will vary with the volume of air within the chamber, and the velocity of the incoming air. Preferably, the temperature measurement within the chamber is made by a standard thermocouple probe attached to a fine wire.

During Step II, the forced injection of air into the chamber 24 is stopped, and continuous weight measurements of the object 20 are taken over the next 10 seconds. The average of these readings is computed and displayed as the high temperature weight of the object. The high temperature weight is preferably calculated after the forced injection of warm air has ceased since the turbulence resulting from the air injection would adversely affect the accuracy of weight readings taken at that time. It is noted that during Step II of the procedure, a cover may be placed over the opened end of passageway 26 to further isolate the heated air within the chamber 24 and the cooler ambient air outside of the chamber.

Step III of the measurement procedure includes the removal of a cover of the chamber 24 to fully expose the object 20 to ambient air temperature. Ambient air is allowed to naturally circulate around the exposed object for approximately 10 seconds. Thereafter, during Step IV of the procedure, the exposed object 20 is weighed continuously over another 10 second time interval, and the average of these readings is computed to be a designated weight at ambient.

It is apparent from a comparison of the weight of the object at elevated air temperature (Step II) with the weight of the object at ambient temperature (Step IV), the weight of the object is greater at the elevated temperature as a result of the lesser buoyant force exerted on the object by the heated (and thus less dense) surrounding air. The difference in the apparent weight of the object at the warmer and cooler air enables a calculation of the buoyant force exerted by the air on the object, which enables a determination of the volume and density of the object, as previously explained, and further illustrated in the Appendix. When the object of the measurement is living tissue, the calculated density thereof is monotonically related to the fat content.

The procedure illustrated by FIG. 2 employs the forced injection of heated air (having a temperature greater than the ambient air temperature) into the chamber 24. However, it is equally within the scope of the invention to inject air at a temperature lower than the ambient air temperature surrounding the object. The apparent weight of the object 20 during Step II of the procedure will be less than the weight of the object at ambient as a result of the greater density and thus greater buoyant force of the cooler injected air acting on the body 20. In either event, the difference in the apparent weight of the body or object is used to calculate the buoyant force exerted by the air on the body or object, and thereby calculate its volume and thus its density.

The steps illustrated by FIG. 2 constitute the basic procedure and operation of the apparatus of the present invention. However, the portion of Step I of the procedure in which the weight of the object is measured at ambient temperature may be eliminated because this same measurement is made during Step IV at the end of the procedure. The weight measurement at ambient taken during Step IV is more significant than the same measurement taken at Step I where the object to be measured is a living body or living tissue because the actual weight of the object may slightly change during Steps I-III as a result of respiration, evaporation or perspiration, and other changes particular to living tissue.

In addition to the above, measurements of different parameters may be periodically taken. For example, where increased accuracy of measurement is desired, the barometric pressure and relative humidity of the ambient air can be measured at periodic intervals, as for example on an hourly basis.

Additionally, Steps I-IV can be run periodically with no object on the scale. The scale components themselves are subject to the buoyant effect of the ambient air. While the scale can be adjusted to a null reading at one temperature and pressure (e.g., at ambient conditions), there is an off-set to the change in the buoyant force exerted on the scale after the hotter or colder air has been injected into the chamber. By running the procedure with no object on the scale, the effect of the change in buoyant forces exerted on the scale by the air at difference temperatures can be measured and thereby compensated for in the calculation of the buoyant forces exerted on the object placed upon the scale.

In all, at least ten different parameters may be measured, depending upon the accuracy of the density calculation which is desired. These different parameters are (1) ambient air temperature within the measuring area or chamber; (2) the temperature of the hot or colder air injected into the measuring area or chamber; (3) the temperature of the hot or colder air exiting from the measuring area or chamber; (4) the initial object weight surrounded by ambient air; (5) the apparent object weight surrounded by the hot or cold injected air; (6) the final object weight surrounded by ambient air after the hot or cold air has been removed; (7) barometric pressure; (8) relative humidity of the air; (9) the reading on the scale with no object placed on it when the scale is surrounded by ambient air; and (10) the reading of the scale with no object placed on it when the scale is surrounded by either the hot or cold injected air. Preferably, measurement numbers (2) and (3) are averaged to determine the true temperature of the hot or cold injected air, and measurement numbers (4) and (6) are averaged to determine the true object weight in ambient air. The relationship between these parameters, and the manner in which they are used to calculate the density of an object being measured, is illustrated in the Appendix attached hereto.

In addition to the above measurements, it is also possible to account for changes in volume of the subject as a result of expansion or contraction due to the injection of the hotter or colder air. Compensation for expansion or contraction can be made by consideration of the coefficient of thermal expansion of the subject under measurement, which is a known value. However, for the vast majority of volume and density measurements made in accordance with the present method and apparatus, the relatively small temperature differential applied to the subject for the relatively short period of time it is applied results in negligible expansion or contraction which can be disregarded in the volume and density calculation.

The above procedure for determining density measurement employs air as the ambient medium, and also as the heated and cooled injected medium. It is within the scope of the invention to employ other gases, as for example inert gases, as the surrounding medium and for the injected medium. The use of air is the preferred medium because of the abudant and ready supply of air, and because living subjects may be surrounded by air without any harmful effects. The use of a gas other than air would increase the cost and complexity of the procedure by requiring a separate supply and source of another gas, and by requiring exclusion of all other gases from the measuring region.

The apparatus and method of the present invention may include air or gas evacuation equipment, such as a fan, instead of relying upon natural air evacuation and diffusion. Moreover, although the measurements taken using the apparatus disclosed by FIGS. 1 and 2 employ a closed or partially closed measurement chamber, it is further within the scope of the invention to take the measurements in an open area. For example, forced hotter or colder air may be blown directly on the object to be measured in the position of the object shown in Steps III and IV of FIG. 2. An open measurement procedure may be employed where the density calculation need not be made with accuracy since the failure to isolate the object being measured will effect the precision of the measurements taken. However, since "normal" room air currents limit sensitivity of weighing a 100 gram object to about one part in 10,000, and a person is about 100,000 grams in weight, the precision of a weight measurement in an open area may still be better than one part per million, thereby enabling the technique of the present invention to be used by merely blowing hotter or colder air at the object in an open area and not surrounding the object in a bath of air within a closed chamber.

In the optimal implementation of this method, it is important to distinguish between two characteristics of a weight measurement; these characteristics are precision and accuracy. The accuracy of a measurement is the fractional error by which the measurement can deviate from the correct measurement. The precision of a measurement is the fractional error of the measured value that is present when repeated measurements are made under similar conditions. Typically, small accuracy values are more difficult to achieve than small precision values.

In this application, the apparatus should produce a density (fat content) measurement to a specified accuracy. As shown in the attached Appendix, this requires that the weight measurement to be made to that same specified accuracy. However, the precision of the weight measurement needs to be the specified accuracy times the ratio of the densities of the fluid and the body, and times the ratio of the absolute fluid temperatures to the change in fluid temperature. For example, typical values require that the repeatability error (the precision) be 20,000 times smaller than the asbsolulte error (the accuracy).

In making the required weight measurements in accordance with the method of the present invention, the absolute weight of the object is not as significant as the difference in weight of the object at ambient air temperature and at the changed air temperature. It is this difference in apparent weight which reflects the buoyant force exerted by the air on the subject. Scales (i.e., G-meters, such as the LaCoste or Romberg type) currently exist to measure variations in the force of gravity and have precisions of about a part per million. The use of a measuring device of such precision (a part per million accuracy) in conjunction with the method and apparatus of the present invention would measure density to an accuracy of 0.1%. Generally speaking, the accuracy of the weight measurement of the object need only be as precise as the required accuracy of the density measurement. For example, a density measurement of 2% accuracy requires an absolute weight measurement having a 2% accuracy and about a 0.0001% precision. The weight measurement of the present invention is ideally suited to a two stage scale in which the first or low resolution measurement stage (accomplished by a balance spring) determines the accuracy of the weight of the object, and the second stage (accomplished by electronic feedback) determines the precision. Preferably the second stage will have a precision, not a accuracy, of about a part per million.

At the precisions discussed above, the weight readings of macroscopic objects, including human beings, drift with time. To compensate for such drifts, it is advisable to make several different weight readings at several different ambient temperatures (reflecting different densities of the surrounding air) to compensate for system drifts, changes in weight due to perspiration of a human subject, air currents, and mechanical creep.

As noted above, the absolute weight measurement error need not be as small as the precision of the weight measurements.

In addition to the above, when the object being measured is a human being, breathing results in variations in the average body volume. In order to compensate for such variations, a series of repeated measurements is made preferably to determine the apparent density of the subject over a time constant approximately equal to the respiration rate of the subject. In the alternative, the calculation of the density of the subject may be made several times in accordance with the procedure discussed above, with the final density value being determined as the average of the several density calculations. Making a series of different density calculations also tends to normalize and compensate for density variations due to the change in buoyancy on the components of the scale apparatus itself to provide a more precise and accurate overall density calculation of the subject being measured.

The weight measurements taken in accordance with the invention described herein may be the absolute accurate weights of the object being measured. However, using such accurate absolute weight values may increase the complexity and cost of the implementation of the device. More specifically, employing absolute weight measurements requires at least two separate and highly accurate weight measurements, one of which is taken at the first known temperature of the surrounding gas medium and the other of which is taken at the second known surrounding temperature. In many instances (depending on the actual weight of the subject of the the measurement and the two different temperatures at which the subject is weighed), the change in apparent weight of the subject will be so slight that accurate absolute weight measurements would be impractical.

To overcome this potential difficulty, it is within the scope of the present invention to calculate the change in buoyant force acting on the subject without measuring its absolute apparent weights. As noted above, the change in buoyant force necessary to determine the volume of the subject is reflected by the change in weight of the subject, and not by either of the absolute weights. Therefore, the subject to be measured may be placed upon a scale to set a base or reference value at a first known temperature; the value need only be precise, not accurate. As the temperature of the surrounding gas medium is changed, thereby changing the buoyant force exerted on the subject and its apparent weight, the scale measures only the difference in weight from the base value, but not the absolute second weight. In this manner, the difference in weight of the subject at the different surrounding gas temperatures may be calculated with a very small error in precision, albeit with a much larger error in accuracy.

The advantage of the above alternative is that it avoids the necessity of ever making a weight measurement with a small error in accuracy. The change in buoyant force and thus the volume of the subject may be determined from the direct weight differential measurement. The final density calculation is made from the ratio of actual weight of the subject to its calculated volume. However, the absolute weight measurement needed for this last calculation need not be made with any high degree of accuracy because this measurement is not employed in the calculation of sensitive weight differences.

As already referred to above, the density of a human subject is directly related to the fat content of the subject. Dieticians, sports therapists, obesity specialists, and other clinical workers have developed standard techniques for inferring body fat composition by comparing a subject's weight under water with this weight in air (see Katch, A. S., et al., "Estimation of body volume by underwater weighing; description of a simple method.", *Journal of Applied Physiology*, 23-811, 1967; "Goldman, R. F., and Buskirk, E. R., "Body volume measurements by underwater weighing: Description of a method", in Brozek, J., and Henchel, A. (eds): *Techniques for Measuring Body Composition*, Washington, D.C., National Academy of Science, 1961. Additionally, formulas are known to calculate the percent body fat of a person (Siri, W. E., "Body composition from fluid spaces and density", University of California Report, Donner Laboratory of Medical Physics, 1978).

It is apparent that increasing the fat content of a body will decrease its density. Fat is mostly oil, and oil floats on water. An obese person will float vertically in a swimming pool with a substantial amount of their shoulders extending above the water, while a lean person will sink if air is expelled from their lungs. Accordingly, a comparison of the density of a human subject in accordance with the method described herein inherently provides a comparison of the fat content of the subjects. The more dense the subject, the less is the fat content of that subject.

It is evident that the method and apparatus of the present invention advantageously enables the volume and density of an unknown subject to be calculated in a single pre-existing, non-invasive medium by merely varying the temperature thereof. The method relies primarily on weight differential measurements. It is particularly useful for measuring porous subjects or subjects with flaws in which immersion measurement techniques would adversely affect the volume of the subject. The method is equally applicable to living subjects, tissue of living subjects, or inanimate articles.

Other advantages and modifications of the method and apparatus will be apparent to those skilled in the art. The description provided herein has been intended to be illustrative only and not restrictive of the scope of the invention, that scope being defined by the following claims and all equivalents thereto.

APPENDIX I

Calculation of Density, with Analytic Estimate of System Errors

We calculate the density of a body from experimental measurements of the body's weigh surrounded by hot air, surrounded by cold air, of the barometric pressure, humidity, and of the air temperatures.

First we define a few variable names, and assign typical values.

| | | |
|---|---|---|
| $\rho_b:$ | $= 1$ | Density of the body (grams per cubic centimeter) |
| $\rho_a:$ | $= 0.0012$ | Typical room temperature air density (grams per cubic centimeter) |
| $\rho_s:$ | $= 4$ | Density of the scale structures (grams per cubic centimeter) |
| $W_c:$ | $= 87500$ | Weight of body at ambient (cold) temperature (grams) |
| $w_c:$ | $= 3600$ | Weight of support only at ambient (cold) temperature (grams) |
| $V_b:$ | $= 87500$ | Volume of body (cubic centimeters) |
| $V_s:$ | $= 1000$ | Volume of support (cubic centimeters) |

(All scales have a support structure made of platforms, pivots, and so forth, and these components are included in this measurement. It is important, because the buoyancy effects on these componcnts can affect the final measurement.)

| | | |
|---|---|---|
| $W_h:$ | $= 87508$ | Weight of person at higher temperature (grams) |
| $w_h:$ | $= 3999$ | Weight of support only at higher temperature (grams) |
| $T_c:$ | $= 293$ | Ambient (cold) temperature, (degrees Kelvin) |
| $T_h:$ | $= 318$ | Elevated temperature, (degrees Kelvin) |
| $B:$ | $= 758$ | Barometric pressure (mm · Hg) |
| $H:$ | $= .3$ | Relative humidity (%/100) |
| $\sigma_w:$ | $= W_c \cdot 5 \cdot 10^{-7}$ | Standard deviation of weight (kilograms) |

(We assume that the scale has been designed to measure small changes in weight to high accuracy, evey though it may have only moderate accuracy for absolute weight measurements. We assume that the weighing errors form a random gaussian distribution.)

| | | |
|---|---|---|
| $\sigma_t:$ | $= 0.2$ | Standard deviation of temperature (degrees Kelvin) |
| $\sigma_b:$ | $= 1$ | Standard deviation of pressure (mm · Hg) |
| $\sigma_h:$ | $= 0.3$ | Standard deviation of humidity (%/100) |

We will need to calculate the effective density of the air from the temperature, barometric pressure, and humidity. We do this using three constants.

$$C_1: = 0.0012929 \frac{273.13}{760} \text{ constant (gm./ml. mm.Hg)}$$

$$C_2: = -7.566 \text{ constant (100*mm.Hg/\% humidity)}$$

$$C_3: = 0.4539 \text{ constant (mm.Hg)}$$

A scale in room temperature air will have some unloaded reading of $$w_c := V_s[\rho_s - \rho_a]$$

When the temperature of the air is raised, the density drops. An approximate relation between the temperature, pressure, and humidity is given by $$\rho_a: = \frac{C_1}{T_c} [B + C_2 H + C_3]$$

The density of air at the elevated temperature would be $$\rho_{ah}: = \frac{C_1}{T_h} [B + C_2 H + C_3]$$

When heated air surrounds the componcnts of the scale such as the pan or platform, the buoyancy effect of the air is reduced, and the scale will read a higher weight:

$$w_h := V_s[\rho_s - \rho_{ah}]$$

$$w_h - w_c = 0.095 \text{ grams}$$

When a body is placed on the scale at the ambient temperature, it weighs $$W_c := V_b[\rho_b - \rho_a] + w_c$$

and in the warmer air it weighs $$W_h := V_b[\rho_b - \rho_{ah}] + w_h$$

The above relations give four equations in four unknowns. When they are solved for the density of the body in terms of the measureable quantities, the result is $$\rho_b := \frac{\frac{W_c - w_c}{T_h} - \frac{W_h - w_h}{T_c}}{W_c - w_c - W_h + w_h} C_1[B + C_2 H + C_3]$$

Notice that all weights appear as the difference between the high and low temperature equivalent measurements. This is why the absolute accuracy of each weight measurement is not critical.

Given that it is possible to make a density measurement from weight measurements at different ambient air temperatures, it is useful to see how accurate the measurement it. This is done by taking the total derivative of the calculated density with respect to each measured variable by the sum rule, squaring the total derivative, and disguarding the cross terms (this assumes that the measurement errors are not correlated). The average of the square of the total derivative is the square of the deviation of the computed density. The pythagorian sum of the products of the squared partial derivative with respect to a variable times the squared standard deviation of that measured variable is equal to the deviation of the computed density.

To simplify the fomulas, we define two variables as follows:

$$Z_1 := [B + C_2 H + C_3]^2$$

$$Z_2 := [W_c - w_c - W_h + w_h]^2$$

The squared partial derivative of the density with respect to the barometric pressure becomes:

$$\delta\rho_{bB2} := \frac{\rho_b^2}{Z_1}$$

Similarly, the squared derivative of the density with respect to the humidity is:

$$\delta\rho_{bH2} := \delta\rho_{bB2} C_2^2$$

The squared derivatives with respect to the temperature and weight measurements are, respectively:

$$\delta\rho_{bT2} := \frac{C_1^2 Z_1}{Z_2} \left[ \frac{[W_h - w_h]^2}{T_c^4} + \frac{[W_c - w_c]^2}{T_h^4} \right]$$

$$\delta\rho_{bW2} := \frac{2 C_1^2 Z_1}{Z_2^2} \left[ \frac{1}{T_h} - \frac{1}{T_c} \right]^2 [[W_h - w_h]^2 + [W_c - w_c]^2]$$

We can now calculate the standard deviation of the density measurement that is produced by the combined uncertainties in the measurements of the weights, temperature, barometric pressure, and humidity:

$$\sigma_{total} = \sqrt{\sigma_w^2 \delta\rho_{bW2} + \sigma_t^2 \delta\rho_{bT2} + \sigma_b^2 \delta\rho_{bB2} + \sigma_h^2 \delta\rho_{bH2}}$$

For the parameters chosen above, the total uncertainty comes out to be $$\sigma_{total} = 0.016$$

Since tyical densities are on the order of 1 gram per cubic centimeter, the combined errors in this case are about 1.6%.

It is useful to know what fraction of this error comes from each measured variable. For example, if all variables except weight had no errors associated with them, the resulting system error would be $$\delta\sigma_W := \sigma_w \sqrt{\delta\rho_{bW2}}$$

which for the above values is $$\delta\sigma_W = 0.011 \text{ grams per cubic centimeter}$$

Similar relations for the temperature, barometric pressure, and humidity are:

$$\delta\sigma_T := \sigma_t \sqrt{\delta\rho_{bT2}} \quad \delta\sigma_T = 0.011 \text{ grams per cubic centimeter}$$

$$\delta\sigma_B := \sigma_b \sqrt{\delta\rho_{bB2}} \quad \delta\sigma_B = 0.001 \text{ grams per cubic centimeter}$$

$$\delta\rho_h := \sigma_h \sqrt{\delta\rho_{bH2}} \quad \delta\rho_h = 0.003 \text{ grams per cubic centimeter}$$

From these we see that humidity variations are nearly ignorable; errors of 30% relative humidity only produce a third of a percent change in the measured density. Temperature and weight need to be measured with the greatest accuracy.

I claim:

1. A method of determining the volume of an object, the steps of said method including:
   surrounding said object with a known gas,
   weighing said object surrounded by said known gas and measuring the temperature of said known surrounding gas,
   varying the temperature of said known surrounding gas to a first temperature,
   measuring said first temperature and weighing said object at said first temperature,
   varying said first temperature of said known surrounding gas to a second temperature,
   measuring said second temperature and weighing said object at said second temperature,
   determining the differences in weight of said object at least at two of said different measured temperatures of said known surrounding gas, and
   determining the volume of said object from said difference in weight of said object.

2. A method of determining the volume of an object, the steps of said method including:
   surrounding said object with a known gas, weighing said object at a first known temperature of said known surrounding gas, providing a source of said known gas at a first predetermined temperature different from said first known temperature, injecting said known gas at said first predetermined temperature towards said object, and weighing said object at said first predetermined gas temperature, varying the temperature of said source of said known gas to a second predetermined temperature different from said first predetermined gas temperature, injecting said known gas at said second predetermined temperature towards said object, and weighing said object at said second predetermined gas temperature, determining the differences in weight of said object at least at two of said different temperatures of said known gas, and determining the volume of said object from said difference in the weight of said object.

3. The method of claim 2 further including the step of injecting said known gas by a blower.

4. The method of claim 3 further including the step of evacuating said known gas surrounding said object while injecting said known gas towards said object at a different temperature.

5. The method of claims 1 or 2 wherein said second temperature of said known gas is the same as said temperature of said known gas in which said first weight measurement is taken.

6. A method of determining the volume of an object, the steps of said method including:

surrounding said object with a known gas at a first known temperature, weighing said object in said known gas at said first known temperature with a precision weight error of less than $10^{-5}$ and accuracy weight error greater than $10^{-5}$, varying the first known temperature of said known gas to a second temperature different from said first known temperature, weighing said object at said second temperature with a precision weight error or less than $10^{-5}$ and an accuracy weight error greater than $10^{-5}$, determining the difference in weight of said object at said first temperature and at said second temperature, and determining the volume of said object from said difference in weight of said object at said first and second temperatures of said known gas.

7. The method of claims 1, 2, or 6 further including the step of determining the density of said object from the ratio of the weight of said object to the volume of said object.

8. The method of claims 1,2 or 5 wherein said known gas is air.

9. The method of claim 8 wherein said object is a living being.

10. The method of claim 9 wherein said living being has a known respiration rate and further including the steps of weighing said living being at a time interval corresponding to said known respiration rate, and compensating for changes in volume of said living being due to respiration.

11. The method of claims 1, 2 or 5 further including the step of taking each weight measurement over a predetermined time interval and determining an average weight value for each of said predetermined time intervals.

12. The method of claims 1, 2 or 6 wherein said step of determining said volume includes the step of periodically measuring the humidity of said known gas and compensating for changes in said humidity.

13. The method of claims 1, 2 or 6 wherein said step of determining said volume includes the step of periodically measuring the barometric pressure of said known gas and compensating for changes in barometric pressure.

14. The method of claims 1, 2 or 6 further including the step of taking said weight measurements of said object on a scale, taking weight measurements at a said different temperatures of said known gas with said object removed from said scale, and adjusting said weight measurements of said object to compensate for buoyant forces acting on said scale.

15. The method of claims 1, 2 or 6 wherein said steps of weighing said object include the steps of weighing said object in a substantially closed housing.

16. The method of claims 1, 2 or 6 wherein said steps of weighing said object include the steps of weighing said object in an open area.

17. The method of claims 1, 2 or 6 wherein the steps of weighing said object includes the step of weighing said object on a scale set at a null value corresponding to the weight of said object at the temperature of said known gas in which said weight measurement is first taken, and determining a second value corresponding to the difference in weight of said object at a different temperature of said known gas.

18. The method of claims 1, 2 or 6 further including the step of displaying volume, density and fat content of said object.

19. An apparatus for determining the volume of an object, surrounded by a known gas said apparatus including:

means for measuring a first temperature of a known gas surrounding an object, means for weighing said object in said known gas at said first temperature, means for varying the first temperature of said known gas to a first predetermined temperature, means for weighing said object at said first predetermined temperature, means for varying the temperature of said known gas to a second predetermined temperature which is different from said first predetermined temperature, means for determining the difference in weights of said object at least at two of said temperatures of said known gas in which said object is weighed, and means for determining the volume of said object based on the difference in said weights.

20. An apparatus for determining the volume of an object, surrounded by a known gas said apparatus including:

means for weighing said object in a known surrounding gas at a first known temperature with a precision weight error of less than $10^{-5}$ and an accuracy weight error greater than $10^{-5}$, means for varying the temperature of said known surrounding gas to a first predetermined temperature which is different from said first known temperature, means for weighing said object at said first predetermined temperature with a precision weight error of less than $10^{-5}$ and an accuracy weight error of greater than $10^{-5}$, means for determining the difference in weight of said object at said first temperature and said first predetermined temperature of said known gas, and means for determining the volume of said object based on said difference in weight of said object in said first and first predetermined temperatures of said known gas.

21. The apparatus of claims 19 or 20 further including means for determining the density of said object based on the ratio of the weight of said object measured at said first temperature of said known gas and said determined volume of said object.

22. The apparatus of claims 19 or 20 wherein said known surrounding gas is air.

23. The apparatus of claims 19 or 20 wherein said means for varying the temperature of said known gas surrounding said object includes a source of said known gas and conduit means, one end of said conduit means being coupled to said source and the other end of said conduit means terminating proximate to said object.

24. The apparatus of claims 19 or 20 further including a housing for enclosing said object.

25. The apparatus of claims 19 or 20 further including means for calculating the relative humidity of said known gas surrounding said object.

26. The apparatus of claims 19 or 20 further including means for calculating the barometric pressure of said known gas surrounding said object.

27. The apparatus of claims 19 or 20 wherein said means for weighing includes a scale set at a null value corresponding to the weight of said object at a known gas temperature, and said differences in weight of said object at temperatures differing from said known gas temperature are determined with reference to said null value of said scale.

28. The apparatus of claims 19 or 20 further including means for displaying weight, volume and density of said object.

29. The apparatus of claims 19 or 20 further including means for calculating and displaying the fat content of said object when said object is a living being.

30. The apparatus of claims 19 or 20 further including means for averaging each of said weight measurements of said object taken at a different one of said temperatures of said known gas surrounding said object over a predetermined interval of time.

* * * * *

UNITED STATES PATENT AND TRADEMARK OFFICE
CERTIFICATE OF CORRECTION

PATENT NO. : 5,052,405
DATED : October 1, 1991
INVENTOR(S) : J. Samuel Batchelder It is certified that error appears in the above-identified patent and that said Letters Patent is hereby corrected as shown below:

Claim 8, Line 1 ( Column 15, Lines 56 ): Delete "5" and substitute - -6- -.

Claim 11, Line 1 ( Column 15, Line 66 ): Delete "5" and substitute - -6- -.

Signed and Sealed this

Twelfth Day of January, 1993

Attest:

DOUGLAS B. COMER

*Attesting Officer*     Acting Commissioner of Patents and Trademarks